United States Patent
McElhattan et al.

(10) Patent No.: US 6,442,639 B1
(45) Date of Patent: Aug. 27, 2002

(54) DOCKING STATION FOR ENVIRONMENTAL MONITORING INSTRUMENTS

(75) Inventors: Kent D. McElhattan, Pittsburgh; David D. Wagner, Library; Annie Q. Wang; James Skourlis, both of Pittsburgh, all of PA (US)

(73) Assignee: Industrial Scientific Corporation, Oakdale, PA (US)

( * ) Notice: Subject to any disclaimer, the term of this patent is extended or adjusted under 35 U.S.C. 154(b) by 0 days.

(21) Appl. No.: 09/552,034

(22) Filed: Apr. 19, 2000

(51) Int. Cl.[7] .............................. G06F 13/00; G01J 5/02
(52) U.S. Cl. ...................... 710/303; 710/305; 250/345
(58) Field of Search .................................. 710/129, 305, 710/303; 250/73, 95, 134, 137, 96, 345, 324

(56) References Cited

U.S. PATENT DOCUMENTS

| | | | | |
|---|---|---|---|---|
| 3,960,495 A | * | 6/1976 | Tantram | 23/232 |
| 5,324,948 A | * | 6/1994 | Dudar et al. | 250/379 |
| 5,558,752 A | * | 9/1996 | Wang et al. | 204/401 |
| 5,591,974 A | * | 1/1997 | Troyers et al. | 250/336.1 |
| 5,611,909 A | * | 3/1997 | Studer | 205/775 |
| 5,662,143 A | * | 9/1997 | Caughran | 137/884 |
| 5,668,302 A | * | 9/1997 | Finbow et al. | 73/23.2 |
| 6,119,186 A | * | 9/2000 | Watts et al. | 710/104 |

\* cited by examiner

Primary Examiner—Peter Wong
Assistant Examiner—Tim Vo
(74) Attorney, Agent, or Firm—Dennison, Schultz & Dougherty

(57) ABSTRACT

A docking station for use with an environmental monitoring instrument to provide predictive diagnostic information. The docking station is connected, typically via the Internet, to a remote service center, and exposure data, calibration data and diagnostic data are communicated from the instrument to the docking station and from the docking station to the service center. Mathematical analysis of the collected data from all available sources is performed at the service center and predictive warnings are generated to alert the users of potential instrument faults, thus allowing preemptive maintenance. The analysis methods include principle component analysis and other statistical methods, fuzzy logic and neural networks. This docking station can be used with monitoring instruments for water quality, pollution control, indoor air quality and breathing air quality.

34 Claims, 4 Drawing Sheets

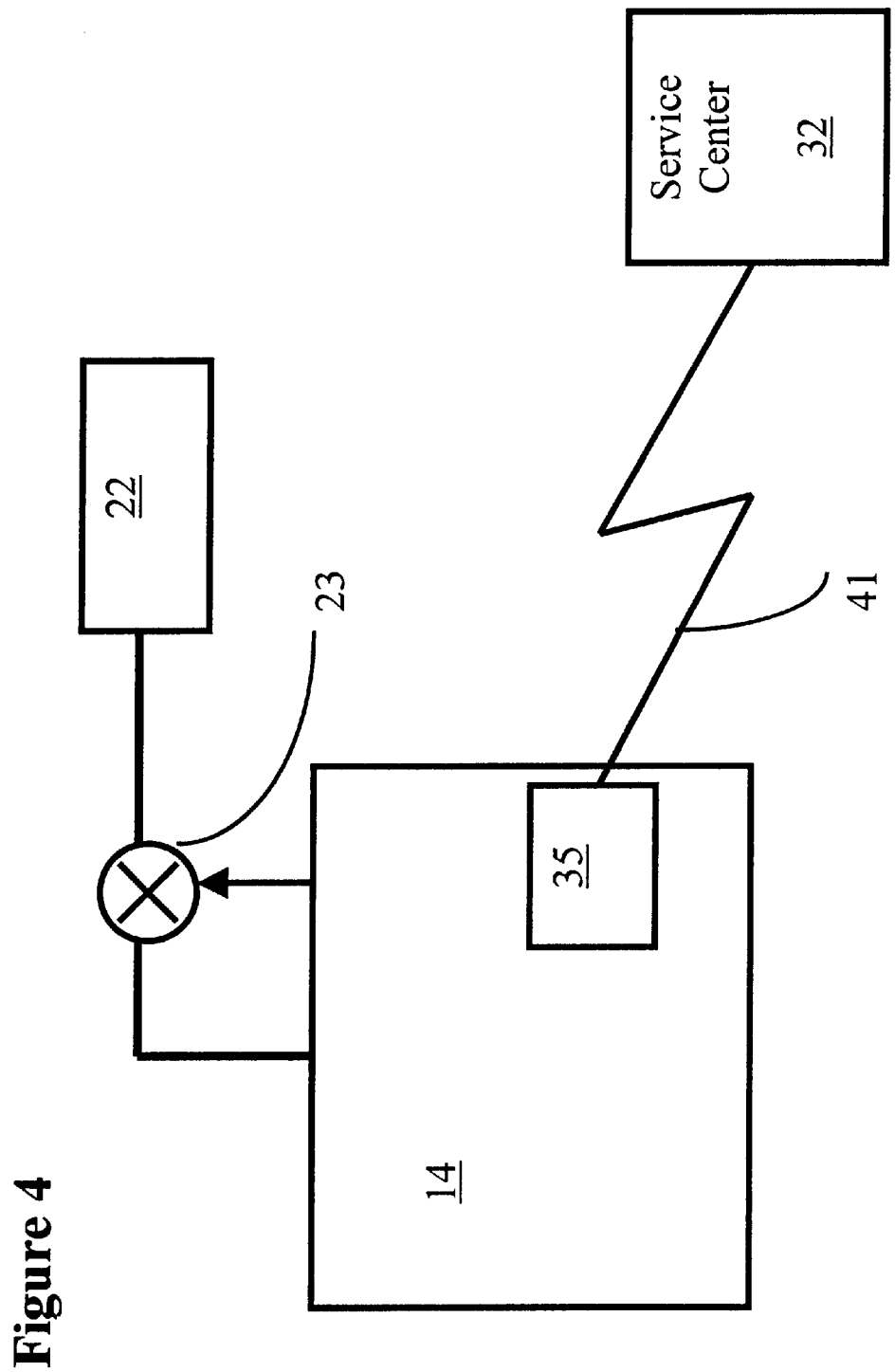

DOCKING STATION FOR ENVIRONMENTAL MONITORING INSTRUMENTS

BACKGROUND OF THE INVENTION

1. Field of the Invention

The present invention relates to a docking station for an environmental monitoring instrument and the interaction between the docking station, the instrument and a service center.

2. Description of Related Art

Potentially dangerous gas mixtures (e.g. combustible gases, toxic gases, excessively high or low oxygen concentrations), noise levels, particulates etc. are found in many work place environments. These dangers are well known and monitoring instruments are available to detect a wide range of potential hazards. Monitoring instruments are also available for other applications including environmental monitoring, such as water quality (e.g. pH, dissolved oxygen, suspended solids, dissolved ions, clarity), pollution control (e.g. volatile organic compounds VOC's, oxides of nitrogen, ozone, particulates etc.), indoor air quality (e.g. carbon dioxide, relative humidity, temperature), and quality of compressed air for a breathing apparatus (e.g. oxygen, carbon monoxide, carbon dioxide, relative humidity). These monitoring instruments typically contain one or more sensors, a signal processing means and output.

For many monitoring applications, if the concentration of the analyte or the magnitude of a physical parameter determined exceeds pre-determined limits, then the instrument may provide an alarm to warn nearby personnel, or it may activate other remedial actions. For example, the instrument may initiate actions such as increasing ventilation or diverting a drinking water stream if the water quality levels are outside of the allowed limits, until the problem is corrected.

Monitoring instruments for safety and environmental applications are broadly divided into two groups, portable instruments which are designed to be hand held or worn by the user, or can easily be transported from one location to another, and fixed instruments which are typically mounted in a fixed location and which provide monitoring at that location.

Monitoring instruments typically contain one or more sensors, which provide an electrical response that varies with the concentration of the analyte or with a parameter being measured. For each sensor, there is associated circuitry for driving the sensor, for measuring and displaying and/or recording the output and for activating visual, vibrational or audible alarms used to notify the user of the presence of a potentially hazardous condition.

Most instruments also contain a microprocessor or other controller and memory features that allow for more complex data analysis, such as industrial hygiene functions. Examples of industrial hygiene functions include calculating time weighted exposure limits, or recording the variation in exposure over time for later analysis. For many toxic substances, especially gases, the time-weighted exposure is as important as the short-term exposure concentration. For example, carbon monoxide has an Immediately Dangerous to Life and Health (IDLH) concentration of 1200 ppm; this corresponds to the maximum concentration of gas from which the average worker can escape without a respirator and without loss of life or irreversible health effects in less than thirty minutes. However, the time weighted average permissible exposure limit (TWA-PEL) to carbon monoxide is only 50 ppm (OSHA); this is the maximum exposure that the average worker can be exposed to for eight hours a day, forty hours a week, repetitively, without adverse effects (NIOSH Pocket Guide to Chemical Hazards, US Department of Health and Human Services, June 1997). Typically, an analytical instrument will store the exposure data for at least one eight-hour shift, and then the data is downloaded to a computer for record keeping and further analysis.

In locations where high concentrations of toxic gases or low concentrations of oxygen are expected, workers may be supplied with a breathable air supply from a compressed gas source. Usually these air supplies incorporate instruments which monitor for toxic and other gases (e.g. carbon monoxide), since if this air supply is contaminated (e.g. by malfunction of the compressor), then it could be very detrimental to the workers who depend on it.

In typical use, a monitoring instrument is calibrated prior to use, a laborious process. Using hazardous gas monitoring as an example, the sensor background outputs are initially set to zero for both toxic and combustible gases by exposure of the instrument to clean air or zero gas. Subsequently, the instrument is exposed to a test mixture, which contains one or more active components of known concentration to which the sensors respond. For calibrating gas sensors, the test mixture is a known concentration of the analyte gas in inert balance gas. For a pH measuring electrode, the calibration may be performed using one or more buffer solutions of known pH as the test mixture. Similarly, other types of sensors will require their own specific test mixtures for calibration. The output of the instrument being calibrated is then set to the known value of the test mixture for each sensor.

The calibration process will vary with each type of sensor and instrument, but all processes involve matching the output of the instrument to a known value, usually a test mixture. For most applications involving safety and environmental monitoring, detailed records of the calibration results are required. The calibration interval depends on the sensor type, the instrument design and on the specific environment in which the instrument is being used. Typically, electrochemical and catalytic gas sensors are calibrated monthly whereas infrared-based gas sensors are calibrated annually. However, there is considerable variation between manufacturers and even instrument models that use similar sensor technology.

Though most sensor technologies are very reliable, as required for safety and environmental applications, sensors do sometimes fail in service. Some sensors, such as galvanic oxygen sensors, are consumed during the oxygen detection reaction and so have a limited lifetime. Many sensors do not have a fixed service life and only fail when a problem develops or the sensor is damaged (e.g. contamination of a pH electrode).

Whereas calibration is usually only performed at fixed time intervals, for many safety and environmental applications it is common practice to "bump test" monitoring instruments to ensure that they are working correctly. The bump test typically involves application of a test mixture to the instrument for enough time to active the warming alarms or other modes of display that indicate that the instrument responded correctly. While the bump test procedure takes less time than a full calibration, it still requires the expense of both time and obtaining a test mixture of known composition.

One area of current development is in-situ diagnostic testing. These tests are performed automatically by the instrument, either with, or preferably without human intervention. Diagnostic methods have been developed for a variety of different sensor types. For example, electrode capacitance methods have been described by Jones in U.S. Pat. No. 5,202,637 and by Studer in U.S. Pat. No. 5,611,909 for electrochemical toxic gases sensors. Parker described a method for galvanic oxygen sensors in U.S. Pat. No. 5,405,512 and Wang et al described a diagnostic method for polarographic oxygen sensors in U.S. Pat. No. 5,558,752. A method for identifying a failing combustible gas sensor has been described by Tantram in U.S. Pat. No. 3,960,495. These diagnostic tests provide the means for evaluating whether critical instrument components, such as the gas sensors are working correctly. Ideally, the instrument, without human involvement, can perform these tests periodically and automatically, and if a component fails the test, then the user is alerted to the problem.

These diagnostic tests have many advantages, such as low cost and automatic operation without human intervention; however in most cases, the best method for testing a sensor is with the intended analyte. For example, a gas sensor should be tested by recording the response of the sensor upon exposing it to the intended analyte gas or a verified substitute. To this end, gas generators have been built into several monitoring instruments; for example, Finbow et al described in U.S. Pat. No. 5,668,302 an electrochemical sensor that incorporated an electrolysis gas-generating cell for bump testing the sensor. Dodgson described a similar device in published PCT application WO 98/25,139. It is likely that automatic diagnostic testing and in-situ test gas generation will become more prevalent in the future.

One of the newest developments in monitoring analytical equipment is the concept of a monitoring instrument docking station. This concept greatly simplifies the existing support necessary for the successful use of a monitoring instrument. The docking station contains a bay into which the monitoring instrument can be mounted, the bay providing means of communication with the instrument. This communication may be via a communications port, infrared link or any other method known in the art. The bay also contains means by which the test mixture can be delivered to the instrument, so that the instrument can be calibrated.

In a typical scenario, when the instrument is mounted into the bay on the docking station, there is bi-directional communication between the instrument and the docking station. This communication may include instrument identification (e.g. serial number) and the current instrument configuration (e.g. alarm levels, identity of installed sensors, software version). The instrument may also download industrial hygiene or data logging results, such as exposure over time etc., to the docking station. The docking station will then calibrate the instrument with the test mixture. In addition to applying the test mixture to the instrument, the docking station must communicate with the instrument that calibration is in progress, receive the resulting test data from the instrument. If the calibration is a success, the instrument is reset for use, and if the instrument fails to calibrate correctly, the user is alerted to the problem.

From the user's standpoint, the use of a docking station greatly simplifies the calibration process. Thus, the user plugs the instrument into a bay on the docking station, and at a later time, when the instrument is retrieved, it is freshly calibrated and ready for use. All of the tedious calibration steps are automated and the record keeping of both the calibration and the hygiene/data logging functions are logged automatically on a personal computer associated with the docking station. The data obtained are available for later retrieval whenever needed.

Examples of currently available docking stations include the TIM—Total Instrument Manager from Mine Safety Appliances Co., Cranberry Township, Pa. 16066 and the IMS—Instrument Management System from Heath Consultants Inc. Houston Tex., 77061. The TIM system provides means to do automatic calibration of gas detection instruments and detection of some existing faults with the instrument. In addition, the system stores the gas exposure and other records locally on the attached computer for later retrieval.

While the introduction of these base-stations constitutes a major advance for users of monitoring instruments, they are still somewhat limited. The instrument performance tests, configuration information and the data logging results are local to the docking station. It is certainly possible for the data to be transmitted to other locations across a network or to more remote locations by standard means, but this requires an additional step and a knowledgeable operator. It also requires pre-planning of where to send the data. For example, if the data is needed at a particular location, the data must be sent to that location. A system whereby the data from a large number of docking stations is automatically sent to a central location, such as a service center would be very advantageous.

The IMS also uses docking stations, and the IMS can connect via a direct line modem to a central database to download gas exposure data, calibration data and diagnostic information. However, the IMS lacks any additional automated analysis of the data to provide a predictive diagnostic capability.

SUMMARY OF THE INVENTION

It is therefore an object of the invention to provide a docking station for environment monitoring instruments that enables automatic retrieval of information from the instrument, and both local and remote analysis of data from the instrument.

To achieve this and other objects, the invention provides a monitoring instrument docking station which can be connected to, or incorporates within, a computer, and one or more bays for interfacing with monitoring instruments. The docking station includes a bi-directional data port which can download information from and upload information to the monitoring instruments, and may also contain means to bump test or calibrate the monitoring instruments. The docking station may also be capable of recharging the instrument batteries, where applicable, and of performing diagnostic tests on the instrument to identify current or future problems or failure. The docking station also contains means to connect, via the Internet, direct telephone or wireless communication, to a service center, which can be located anywhere in the world. The service center maintains a database of the data received from many docking stations and the service center uses software to analyze the data to provide diagnostic data about the monitoring instruments and thus improve their reliability. This analytical software may be based on neural networks, principle component analysis, and other mathematical analysis means, which allow the software analysis to adapt to the data provided by the docking stations and thus maximize the quality of the results obtained.

In a typical embodiment, the service center is a computer connected to the Internet to which a group of docking stations communicate. This service center may be part of the same organization that manages the monitoring instruments and docking stations, or it may be part of an external organization and may be located anywhere in the world. The communication between the docking station and the service center is also bi-directional. The docking station sends identification information about itself, the monitoring instrument's location, time and date etc. It also sends exposure information, the user's name and other information that is required or desired for record keeping. The service center can send software updates, new sensor configurations, requests for diagnostics, information or alerts for the user to be displayed on either the docking station of the monitoring instrument display. The communication between the docking station and the service center may occur at the same time as the instrument is being calibrated, if the docking station is connected to the Internet at that time. Alternatively, the docking station may include data storage means and simply store the information that needs to be sent to the service center until such time as a connection to the Internet is established. The means for sending data files over the Internet are well known in the art, and standard formats can be employed within the scope of this invention.

The docking station typically contains a bay into which the monitoring instrument can be connected. Alternative methods of communicatively coupling the monitoring instrument to the docking station include a cable connection, a jack connector, and an infrared link. Many other methods for transmitting electronic information between electronic devices are well known to those experienced in the art, and these can be substituted for the illustrations provided without limitation on the scope of this invention.

The functional role of the bay is to provide for bi-directional communication between the monitoring instrument and the docking station, and to provide means for the delivery of test mixtures of known composition for the purposes of calibrating and bump testing the monitoring instrument. Alternative mechanical and electrical configurations, which achieve this same result, can be used within the scope of this invention.

The term "environmental monitoring instrument" is intended to apply to a wide variety of fixed and portable instruments, including gas detectors of various types, particulate matter detectors, liquid analysis instruments, and temperature and humidity recording devices. Also within the scope of the invention are devices for monitoring industrial processes.

BRIEF DESCRIPTION OF THE DRAWINGS

The invention will be better understood by reference to the drawings, in which.

DESCRIPTION OF THE PREFERRED EMBODIMENTS

Figure 1:
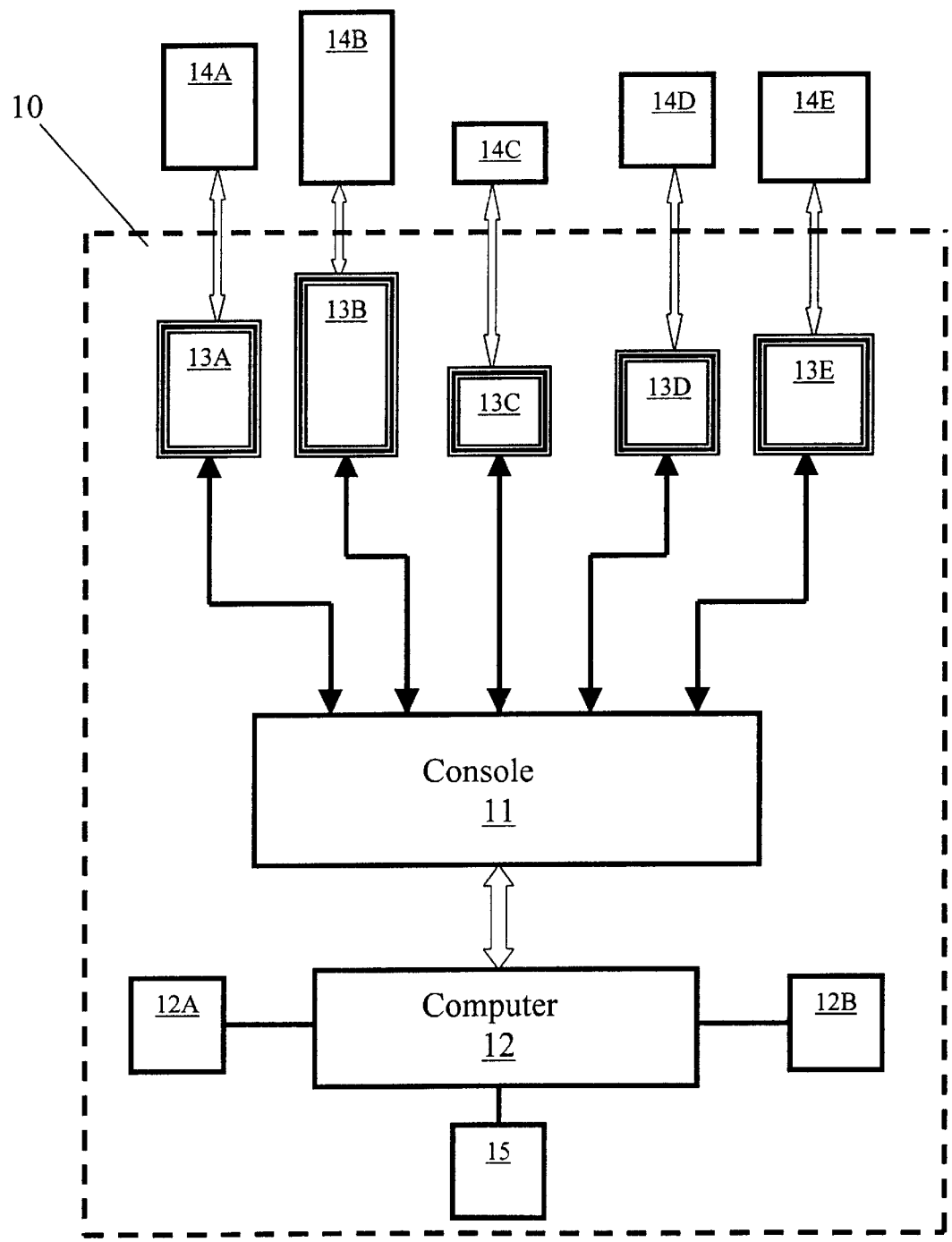
FIG. 1 is a schematic representation of a docking station, connected to multiple bays and monitoring instruments.

The docking stations include four functional components, 1) the bay, as discussed above, 2) a console, 3) a computer with interface to the user and 4) a communications facility. The computer in this case may be a personal computer fitted with a standard internal modem for connection to the Internet. The computer provides the interface with the user, e.g. keyboard, touch screen, bar code etc., for data entry; display panel, lights or graphics display etc. for presenting data to the user in visual form, and the microprocessor capability needed for the docking station.

In one preferred embodiment of the invention, the docking station is adapted to receive portable monitoring instruments of the type that are hand-held or worn. The docking station, for example, located in a work place environment in which there is the potential risk of exposure of personnel to hazardous atmospheres, and protective monitoring instruments are provided for the workers. At the start of a shift, the workers collect their portable monitoring instruments from the docking station, and enter their name and work location into the docking station. This operation may involve typing with a keyboard, touch screen, bar code scanner or iButton (Dallas Semiconductor, Dallas, Tex. 75244) or any other well-known method of data entry. Thus each portable instrument is assigned to an individual. The workers proceed with their business and at the end of the shift, return their monitoring instruments to the docking station. If a worker has been exposed to a potentially hazardous atmosphere during their shift, then the monitoring instrument would have provided an audible, visual and or vibrational warning to alert him or her of the potential risk at the time of the exposure. In addition, if the instrument incorporates hygiene functions, then the instrument would have logged the exposure versus time data.

After returning the monitoring instrument to the docking station, the battery in the instrument is recharged and two-way communication begins between the instrument and the docking station. A log of the gas exposure versus time is transmitted from the instrument to the docking station, together with the instrument identification data, software version, configuration and perhaps identification data and diagnostic data for some of the mechanical or electrical components as well, such as the sensors, and power source. Furthermore, the instrument may have performed diagnostic tests on some of its key components, such as the gas sensors, and the results of these tests may also be transmitted to the docking station. The docking station may instigate this data and perform the diagnostics or the diagnostics may be performed routinely by the instrument and the results reported to the docking station or a combination thereof.

If the configuration requirements have changed, or if a new version of the software is available, the docking station may then proceed to upload the new configurations or software file to the monitoring instrument. The docking station will then either calibrate or bump test the instrument to ensure that it is working correctly. At the completion of this process, the instrument is then ready for use again.

The docking station may also perform some diagnostic tests on the instrument. For example, the docking station may include a microphone that can be used to check whether the audible alarms (if present) are working properly.

The docking station will review the data for any alerts that require immediate or local action, for example, a component such as the battery that failed a diagnostic test and that would need to be replaced, or hygiene data indicating that a worker had been exposed to a reportable concentration of potentially hazardous gas. The docking station would create a file with the instrument data, hygiene data, user name, location, date and other relevant information. Either immediately, or at a later time, the docking station would send the data collected, via the Internet to one or more service centers.

The service center would collate and store all the data files from docking stations from one or more locations, which may be located anywhere in the world. This database could then be used to provide reports on the exposure of workers to potentially hazardous gases or other environmental hazards, which have been monitored, or compare the exposure of personnel working at different facilities. The service center could also perform additional diagnostic analysis on the data received. For example, by tracking how efficiently a battery accepted a charge, the lifetime of the battery may be predicted. This type of long-term tracking would allow the central data docking station to alert the user or other service personnel, most probably via the docking station that the battery should be replaced before it fails.

For a small work place organization in a fixed location, the current art of monitoring is usually adequate. Where the monitoring instruments are used by workers to provide continuous monitoring for environmental or safety hazards, the industrial hygiene or other exposure logs data can be downloaded, and the data saved on the computer at the location of download, or on a network to which that computer is attached. However, for many organizations, this current state of the art is not adequate. For example, large corporations operating at several sites, perhaps in different states or even continents may want to have a standardized and central industrial hygiene repository. Compiling the exposure data from all of the workers at all of the sites presents a very significant challenge. A common docking station, sending data to a central location over the Internet provides a simple solution to this problem.

On a smaller scale, contractors, for example, who work at many different locations, are unlikely to have an accessible central computer system for their industrial hygiene or environmental monitoring data, unless they always return to a common base. With this invention, workers can download the data from their monitoring instruments, reconfigure them as necessary, using a portable or mobile docking station. The docking station will log their exposure data, and this data can be forwarded to the service center at any convenient time either then or some time later.

The connection to the Internet can be made by many methods including modem connection via telephone, cable TV, fiber optic cables or other fixed lines, via a local area network (LAN), satellite or by a wireless modem. These examples are just some of the many ways to connect to the Internet that can be used as is well know to those experienced in the art. Connection via the Internet is the preferred means of communication between the docking stations and the service center; however other methods such as direct dial modem connection can also be used with the scope of this invention.

Another application where this invention will be of value over the current art is for monitoring chemicals or other parameters whose exposure risk depends on cumulative exposure, for example excessive noise, heavy metal compounds (e.g. tetraethyl lead), or suspected carcinogens such as benzene. For personnel who work at many different sites, use of monitoring instruments with the current docking stations is likely to result in the formation of several discrete exposure data files, which will remain separate unless someone actively combines them. Thus, if it were necessary to calculate the total cumulative exposure to the hazardous agent, there is a risk that data files will be missed and the calculated exposure will be lower than the actual value. This potential problem represents an under assessment of the exposure risk for the personnel involved. By use of this invention, the total exposure history for any individual would be obtainable by searching the service center.

The main advantage of this invention over the prior art is convenience to the user. The user can simply place a portable instrument into the bay of the docking station and leave it. The calibration, data downloading, diagnostics etc. are all performed automatically, thus saving the user both time and money.

Another advantage of this invention is the ease with which software upgrades can be achieved. Many monitoring instruments contain a microprocessor for control of the instrument, data collection of processing of the industrial hygiene functions and communications with the docking station. Often, the manufacturer of the monitoring instrument will update the software in the instrument to correct problems that have been identified, introduce new features, change settings or modify the monitoring instrument to comply with new regulations.

In most instruments, a software upgrade is performed by means of opening the instrument and physically exchanging the microprocessor for one with the new program. Recently, programmable microprocessors have become available, such as the ATMega 103L microprocessor from Atmel Corporation, San Jose, Calif. 95131. These microprocessors allow a monitoring instrument to be upgraded by simply uploading a new software program into the instrument from the docking station. Thus instead of recalling all older instruments to upgrade the software, the manufacturer can achieve the same upgrade by simply transmitting the new software via the service center and the docking stations. Thus, this invention allows large numbers of instruments in many different locations to be rapidly upgraded in a matter of hours instead of the conventional months to years.

Similarly, the same problems will be faced by the industrial hygiene or environmental monitoring department of a large multi-site corporation which decided to change the alarm settings or the calibration interval of all of its monitors to a lower level. This process would be quite cumbersome by the conventional method, as each of the instruments would have to be reprogrammed manually, once that location had received the new settings. With the invention disclosed herein, the corporation could modify a single file at the service center location, and this file would then be automatically uploaded into every monitoring instrument that needed it, along with a complete record of the update having been performed.

The instrument settings can also be updated by the user by means of the docking station, without the need for a communication from the service center. Thus, some sensors such as catalytic bead combustible gas sensors can be used to detect a wide variety of gases, each with own relative sensitivity factor to a calibration gas (typically either methane or pentane in air). If it were desired to change the analyte gas, and hence also the sensitivity factor and possibly alarm levels, this change could be performed through the docking station and the new configuration up-loaded into one or more instruments.

In another embodiment of the invention, the instrument is able to communicate bi-directionally with the docking station via wireless means. While the instrument would most likely still be returned to a bay on the docking station for calibration and battery charging functions, the wireless bi-directional communication may be used to alert the user that the instrument is due for calibration or a potential fault has been identified by the service center, or to transmit new instrument settings or software. Many wireless protocols are known that can be used for this application, such as the Bluetooth system available from Motorola Inc., Schaumburg, Ill. and other companies, and the spread spectrum protocol developed by World Wireless Communications Inc., Salt Lake City, Utah. In addition, wireless communication allows continuous and real time communication between one or more instruments and the docking station to accumulate logs of instrument data to be sent to the service center.

In another embodiment of this invention, the docking station communication function can be incorporated into a monitoring instrument. The instrument would then communicate bi-directionally to the service center using standard communication methods known in the art. This communication is preferably via the Internet, but alternative communicative routes may also be used, such as local area networks, direct modem to modem connection etc. The most preferable means of implementing this communication to the instrument is via one of the known forms of wireless communication.

A docking station incorporated into a monitoring instrument may be a separate component that attaches to the instrument or it may be an integral part of the instrument. This docking station would still perform most of the same functions as described herein. The docking station would communicate bi-directionally with the service center, download exposure records, calibration results and diagnostic information. Instrument settings, software updates, user information (e.g. instrument maintenance notification) can be uploaded. The docking station and or instrument can initiate diagnostic tests and either identifies problems within the instrument or relay the results to the service center for interpretation of the results.

An additional advantage of this embodiment of the invention is that it can be implemented for both fixed and portable instruments. Thus for example, an instrument used to monitor water conductivity may be mounted on the side of a water tank and record the conductivity of the water every minute. Every day the instrument can connect to the service center and down load the logged data. The results of diagnostics tests (e.g. for fouling of the electrodes) can also be sent to the service center and changes in the settings uploaded to the conductivity instrument (e.g., to adjust the compensation required to null out the effects of electrode fouling).

The extent to which some of the other features of this invention can be incorporated into the instrument design incorporating the docking station function will depend on the application. For example, most fixed systems use a hard-wire power supply and so it is not necessary to include the ability to recharge the batteries.

One of the advantages of this system is that all the data at the service center is searchable at once, even if it was collected from sites across several continents. This feature allows the industrial hygienist responsible to search complete records rapidly, and immediately, without having to assemble all the data together. Furthermore, this invention makes it relatively simple to have automatic review of the data, both highlighting data that needs closer examination, examining long-term trends, comparing the exposure records of personnel at different sites. The automatic review may identify trends that are developing before they become serious, and forward the information to those people or organizations that need it, thus increasing safety, saving time and reducing cost. The current state of the art does not allow for automatic data searches to be performed even if the data is manually collected at one location, and the task becomes more difficult when dealing with multiple locations, perhaps in different time zones.

In another area of review, if the calibration data and instrument diagnostic data are also transmitted back to the service center, then this data can also be tracked. For example, with some types of sensors, the sensitivity of the sensor slowly decreases with age. When the sensitivity decreases below a minimum specification, then the sensor is deemed to have failed. The rate of fall of sensitivity often depends greatly on the environment in which the monitoring instrument is used. Therefore, the use of statistical process control methodologies or diagnostics tests, or combinations of both, can be used to predict the early failure of a sensor or other component.

By tracking the sensitivity from calibration to calibration, the lifetime of many types of sensor can be predicted. This result allows preventative maintenance, i.e. replacement of the sensor, before the sensor fails. The analysis of the calibration data, in conjunction with diagnostic tests performed by the monitoring instrument on the sensors and other critical components greatly increases the reliability of the instrument.

This analysis may comprise one or more of the many known mathematical techniques employed in subject areas such as chemometrics or the so-called "data mining." These techniques may include, but are not limited to statistical correlations (e.g. linear and multi variate regression and statistical process control methods), principle component analysis, canonical variates analysis, fuzzy logic and non-linear methods of data analysis such as neural networks. Each of these methods has its weaknesses and strengths, and often combinations of them are used.

If there is a very strong and simple correlation between a diagnostic variable and sensor or other component performance, then a simple statistical correlation between the two may be sufficient to provide adequate predictive capability of imminent sensor or component failures. If statistical correlations are found, then these correlations can become the basis for predictive rules.

If simple rules are developed, for example, Boolean logic relationships (e.g. open circuit sensor does not work), then the predictive capability is straightforward. However, if the rules are more complex, (decreases in the electrode capacitance beyond a predefined limit results in a reduction in sensor sensitivity), then a fuzzy logic based predictive system may be more suitable.

If the relationship is even less clear, for example, the failure mode depends on several variables, then methods such as principle component analysis may offer the best solution. Similarly, for complex analysis involving non-linear relationships between multiple variables, neural networks may provide the best method to predict sensor or component failure.

In one embodiment of the invention, the database of the service center includes date of test, sensor sensitivity, exposure records and the results of diagnostics tests on the sensor and the instrument. Eventually, the database will contain the variation in sensitivity and the other measured parameters with time for sensors that are working, some failing and some that have failed. The data will thereby contain sensor and instrument diagnostic data prior to the failure of any sensors, and up to the failure of the sensors. This data set can be analyzed to identify predictors of future sensor failure and to make these predictions.

At the simplest level, some sensors are consumable, so once they have reached a cumulative exposure limit, they need to be replaced. A simple analysis of the exposure data and the calibration data for these sensors can be used to provide notification to the user that the sensor should be replaced.

In a more complex example, artificial neural networks have been found suitable for the analysis of a data file of sensor output and sensor and instrument diagnostic results over time. In a typical configuration, a three layer neural network comprises an input layer, with a node for each input, a hidden layer and an output layer, with a node for each output is used. Part of the sensor sensitivity and diagnostic data is selected and used to train the neural network, by modifying the weights of the connections between the nodes using a standard back propagation algorithm. The neural network can then tested with the remainder of the diagnostic data and once the reliability of the neural network has been confirmed, predictive results can then be obtained from currently working sensors. If the neural network predicts that a sensor is about to fail, then a warning can be transmitted back to the docking station for the user of the monitoring instrument. Many configurations of neural network are known, and the embodiment of the invention described above is intended to illustrate the application of neural networks in this invention and is not intended to limit the scope if this invention.

Over time more data will be collected at the service center and so the analysis models will be improved. This improvement will allow more reliable use of the predictions based on the analysis of sensor and instrument diagnostic tests. The data analysis software preferably contains several methods of analysis, such as those illustrated above. The software also should have means to evaluate the data to determine which analysis method is the most suitable and selecting this method for the analysis.

In practice, it is beneficial to use a combination of analysis methods. For example, in most cases, not all of the diagnostic data will be correlated with the failure of a sensor or other component. This additional non-correlated data simply introduces noise into the analysis. Principle component analysis can be used to "prune" those data components that do not have any contribution, and then a subsequent neural network analysis or other analysis method will give a more reliable result compared to using the complete data.

These methods of analysis are examples of the many well-known analysis techniques in the art of mathematics, chemometrics and other methods of analyzing data can be used within the scope of this invention.

Obviously, many variations in the format of the docking station, the monitoring instrument, the method of communication between them and in the information thus communicated can be envisioned by those experienced in the art of communication between electronic devices, based upon this application. Similarly, many variations in diagnostics tests on the sensors and other key components are known or can be developed and many techniques are available for the analysis of this data. Such variations should be considered within the scope of this invention and the illustrations used above are intended to illustrate the concepts of this invention without limiting the scope of the invention.

A first preferred embodiment of the invention is shown in FIG. 1, in which a docking station 10 includes a console 11 and a plurality of bays 13A to 13E, each designed to interface with a respective monitoring device 14A to 14E. The bays are connected to a console 11 which is connected to a computer 12, which provides means for data display 12A and means for data entry 12B by the operator. These data display and data entry means are conventional, for example a monitor and keyboard respectively. In addition the computer 12 also incorporates output means 15 for communication to a remote location.

In its actual physical embodiment, the console 11 and computer 12 may be a single unit or may be in separate interconnected units. Similarly, the bays 14A–14E may be part of the console or may be separate therefrom and connected thereto by cable or infra-red communication.

Since there are many designs of monitoring instruments, each of the bays 13A to 13E will be adapted to match the characteristics of one or more of the instruments. Thus, instrument 14A may be designed to detect a toxic gas, whereas instrument 14B may be designed to detect particulates. The bays 13A and 13B may be designed to be used by more than one type of instrument 14, or alternatively each instrument type 14 can have its own type of bay 13. The console 11 is designed to accept one or more bays 13, such that the number of bays 13 used in the base unit 10 can be adjusted depending on the requirements of the user.

Figure 2:
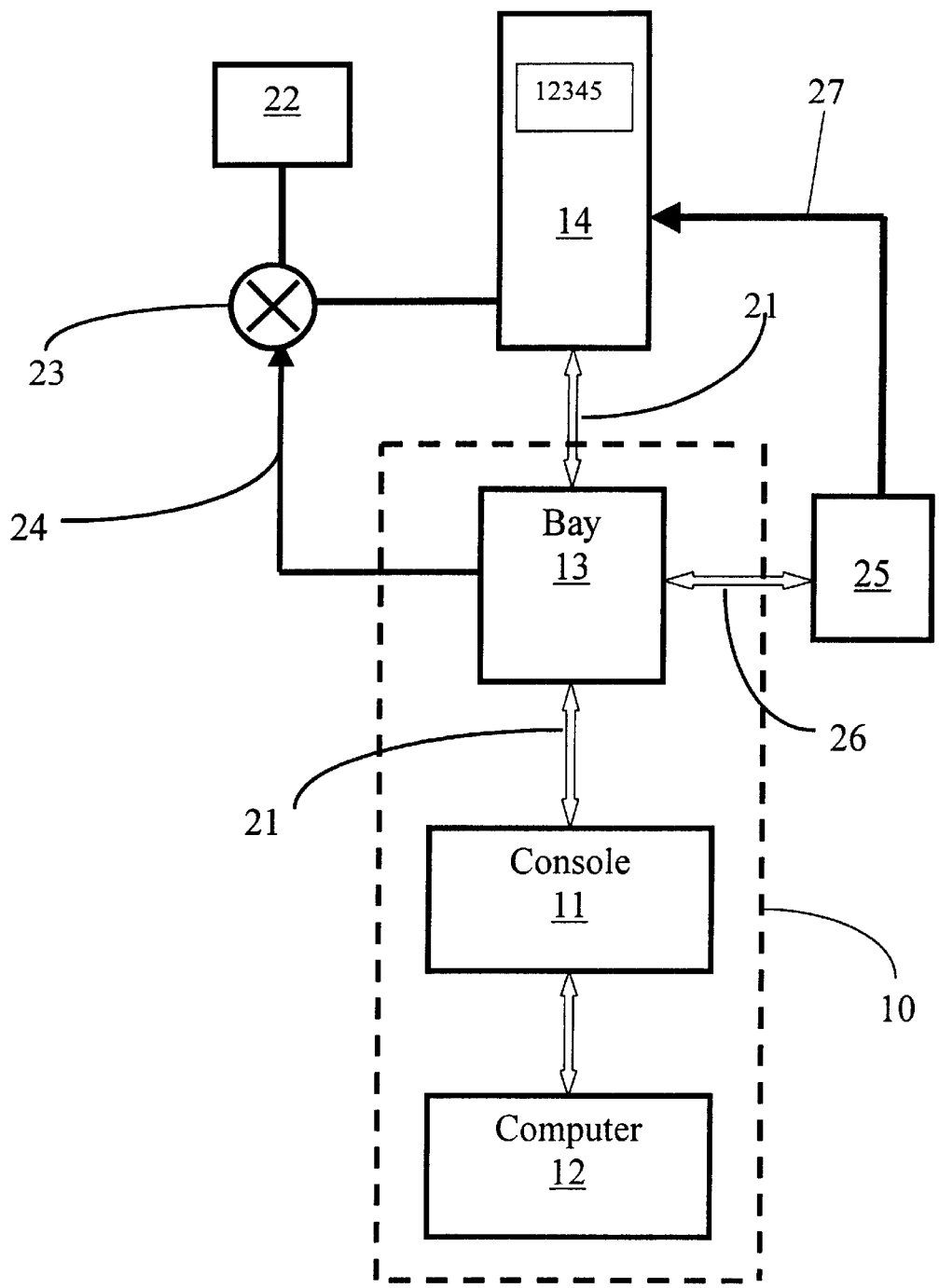
FIG. 2 is a schematic representation of a typical monitoring instrument, bay and docking station.

FIG. 2 shows a monitoring instrument 14 connected to a single bay 13, which is connected to the console 11 and computer 12 comprising part of the docking station 10. There is bi-directional communication between the console 11, the bay 13 and the monitoring instrument 14, represented by the double-headed arrows 21. Typically, data is downloaded from the monitoring instrument 14 to the console 11 and instrument configuration changes or software updates may pass from the console 11 back to the instrument 14.

In addition, a test mixture source 22 is provided for calibrating or bump testing instrument 14. The supply of the test mixture from the source 22 to the instrument 14 may be regulated via valve 23, which is controlled by the console 11 via control line 24 and bay 13. Valve 23 may be a solenoid valve, mass flow meter or other appropriate means for controlling a test mixture as is well known in the art. The test mixture will vary with the type of sensor. For example, if the instrument 14 contains one or more gas sensors, the test mixture will be a gas of known composition such as a compressed gas cylinder or a gas generator. Obviously, for other kinds of monitoring instrument and sensors, alternative test mixtures and means of delivery would be used.

Since test mixtures are often expensive, simpler bump tests are often performed on instruments between calibrations. Typically the time of exposure is less than used for a calibration, and often the accuracy requirements of the test mixture for a bump test are less than for calibration and thus the cost is lower. The bump test and calibration may be performed using the same source 22; alternatively, an additional test mixture container 22 (e.g. cylinder), valve and control line may be used to provide gas for the bump test.

Furthermore, if the monitoring instrument operates from batteries, the docking station 10 may also recharge the batteries. Typically the bay 13 contains or is connected to a charger 25 suitable for the instrument 14 in the bay, and the charger 25 is connected to the monitoring instrument 14 by wire, jack or other connector 27. The type of charger used will depend on the number of batteries used, the battery type and charging regime required. The charger may be controlled by console 11, typically via the bay 13, and communication line 26, or it may function upon connection to the instrument. It is advantageous to have the console 11 able to either control and monitor the charging process or communicate bi-directionally with the charger 25, since the charging data can be used to diagnose the functional status of the monitoring instrument battery.

Thus, the next time the instrument 14 is used, it will have been bump tested or calibrated, had its batteries recharged as applicable, its previous exposure data downloaded and any new instrument software or settings uploaded.

In FIG. 2, the functional units of the bay 13, the bi-directional communication 21, control of the test mixture via control line 24 and valve 23 and the battery charger 25 are shown as separate components for clarity. While the use of separate components is adequate, it is preferable if most or all of these functions are incorporated into a single bay unit 13.

Figure 3:
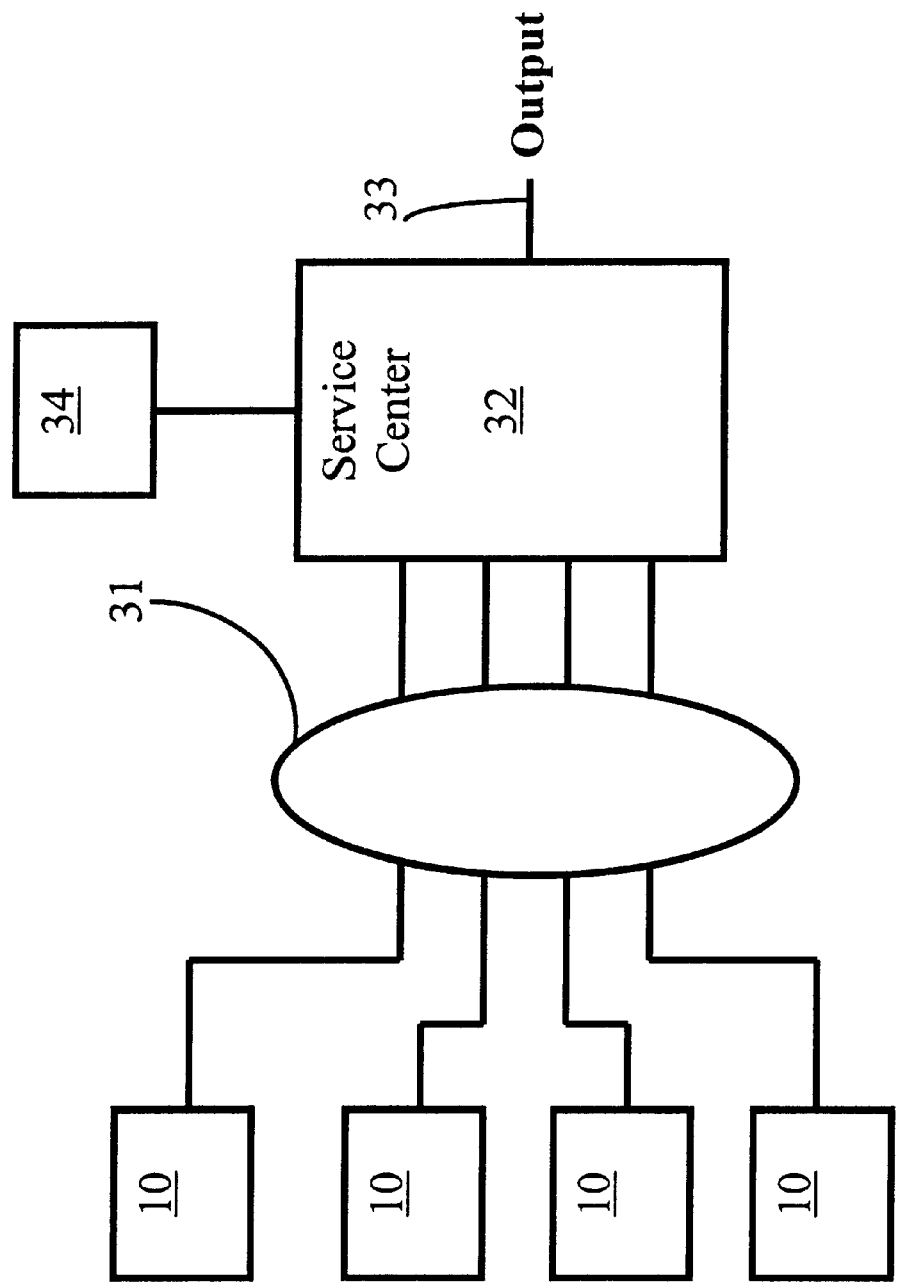
FIG. 3 is a schematic representation of a central control station connected to multiple docking stations via the FIG. 4 is a schematic representation of a monitoring instrument with bi-directional communication facility.

FIG. 3 shows a plurality of docking stations 10 according to the invention, which communicate via the Internet 31 with a service center 32. The docking stations 10 shown in FIG. 3 are representative of a large number of docking stations which may be located anywhere in the world. The communication between the docking stations 10 and the service center 32 is also bi-directional. The data from a monitoring instrument connected to the docking station will be transmitted from the docking station 10 to the service center 32. In addition, any instrument configuration changes or software updates can be sent from the service center 32 to the docking station 10 to be uploaded into the instrument 14.

The service center 32 includes an output 33 and storage media 34 containing a database containing the data received from the monitoring instruments 10. This data is analyzed by software in the service center 32 to extract diagnostic information about the sensors or other key components of the monitoring instruments 14. The output 33 of this analysis is a warning of upcoming failure of a component of a monitoring instrument 14. This warning is also then transmitted via the Internet 31 (or other convenient means) back to the docking station 10 used with that instrument 14 so that this warning can be provided to the user.

FIG. 4 shows an additional embodiment of this invention, in which the monitoring instrument 14 and docking station are constructed as a single unit. Thus, instrument 14 includes computer means 35 with an input device, an output device and a bi-directional communication facility 41, and the monitoring instrument 14 is able to communicate bi-directionally with the service center 32. This communication with the service center is preferably wireless and more preferably over the Internet, though other communication routes may also be employed. Means for wireless communication over the Internet are known in the art, and standard communications methods and protocols can be employed within the scope of this invention.

Means for calibration of the sensors within the instrument 14 by applying a test mixture from a source 22 to the sensors, controlled by valve or other means 23 can also be used with this embodiment. The source of the test mixture source 22 can either be external to the instrument 14, or more preferably, the test mixture source 22 will be contained within the instrument 14. For example, if the instrument 14 is designed to monitor gases, the test mixture source 22 may be an electrochemical gas generator, such as that described by Rohrbacker et al in U.S. Pat. No. 5,395,501.

What is claimed is:

1. A docking station for an environmental monitoring instrument including means for measuring at least one physical or chemical environmental parameter, said docking station comprising:
   means for receiving at least one environmental monitoring instrument;
   computer means including a user interface for input and retrieval of data;
   a bi-directional data port for downloading measured data from the instrument to the computer and uploading data to the instrument from the computer; and
   communications means for connecting the computer means to a remote monitoring station enabling remote download of measured data from the instrument and remote upload of data to the instrument.

2. A docking station according to claim 1, additionally comprising means for recharging a rechargeable battery disposed in the instrument.

3. A docking station according to claim 1, wherein the communications means is adapted for connection to the Internet.

4. A docking station according to claim 1, wherein the user interface includes a keyboard, touch screen or bar code reader for input of information, and a monitor or display panel for retrieval of information.

5. A docking station according to claim 1, wherein the computer means includes data storage means for storing data received through the data port.

6. A docking station according to claim 1, wherein the receiving means comprises at least one bay.

7. A docking station according to claim 1, wherein the receiving means comprises a jack, a cable or an infra-red communication device.

8. A docking station according to claim 1, additionally comprising means for calibrating the instrument, means for bump testing the instrument or both means for calibrating and bump testing the instrument.

9. A docking station according to claim 1, wherein the bi-directional data port comprises means for uploading instrument settings and software from the service center to the instrument.

10. A docking station according to claim 8, wherein the instrument includes means for gas analysis, and the means for calibrating or bump testing includes a source of test gas and a valve through which the source is connected to the docking station.

11. In combination,
   an environmental monitoring instrument including means for measuring at least one physical or chemical environmental parameter, and
   a docking station connected to the environmental instrument, the docking station comprising means for receiving at least one said environmental monitoring instrument, computer means including a user interface for input and retrieval of data, a bi-directional data port for downloading measured data from the instrument to the computer and uploading data to the instrument from the computer, and communications means for connecting the computer means to a remote monitoring station enabling remote download of measured data from the instrument and remote upload of data to the instrument.

12. The combination according to claim 11, wherein the instrument comprises a rechargeable battery, and the docking station comprises means for recharging the battery.

13. The combination according to claim 11, wherein the communications means is adapted for connection to the Internet.

14. The combination according to claim 11, wherein the user interface includes a keyboard, touch screen or bar code reader for input of information, and a monitor or display panel for retrieval of information.

15. The combination according to claim 11, wherein the computer means includes data storage means for storing data received through the data port.

16. The combination according to claim 11, wherein the receiving means comprises at least one bay in which the instrument is disposed.

17. The combination according to claim 11, wherein the instrument is physically separate from the receiving means and is communicates therewith by a cable or an infra-red device.

18. The combination according to claim 11, additionally comprising means for calibrating the instrument, means for bump testing the instrument or both means for calibrating and bump testing the instrument.

19. The combination according to claim 11, wherein the instrument and docking station are combined into a single unit.

20. The combination according to claim 11, wherein the instrument contains means to perform a function selected from the group consisting of gas analysis, liquid analysis, particulate monitoring, temperature monitoring and humidity monitoring.

21. The combination according to claim 11, wherein the bi-directional data port comprises means for uploading instrument settings and software from the service center to the instrument.

22. The combination according to claim 18, wherein the instrument includes means for gas analysis, and the means for calibrating or bump testing includes a source of test gas and a valve through which the source is connected to the docking station.

23. A method for operating an environmental monitoring instrument including means for measuring at least one physical or chemical environmental parameter, comprising the steps of:
    operatively connecting the instrument to a docking station comprising means for receiving at least one said environmental monitoring instrument, computer means including a user interface for input and retrieval of data, a bi-directional data port for downloading data from the instrument to the computer and uploading data to the instrument from the computer, and communications means for connecting the computer means to a remote monitoring station;
    downloading measured data from instrument to the docking station;
    establishing communication between the docking station and a service center remote therefrom;
    transmitting said downloaded data from the docking station to the service center;
    transmitting information dependent on the transmitted data from the service center to the docking station; and
    uploading the transmitted information from the docking station to the instrument.

24. The method according to claim 23, wherein the communication is established via the Internet.

25. The method according to claim 23, wherein the docking station includes means for calibrating or bump testing the instrument, calibration or bump test data is transmitted to the remote service center, and diagnostic conclusions are transmitted to the docking station and uploaded to the instrument.

26. The method according to claim 23, wherein the instrument includes rechargeable batteries and the docking station recharges said batteries and provides data related to the recharging to the remote service center, and the remote service center transmits information relative to battery life to the docking station.

27. The method according to claim 23, wherein the service center transmits instrument settings or software to the docking station, and the instrument settings or software are uploaded to the instrument.

28. The method according to claim 23, wherein the data transmitted to the remote service center is subjected to analysis by a method including principle component analysis, neural network analysis, fuzzy logic and statistical methods.

29. The method according to claim 23, wherein the communication is wireless communication.

30. The method according to claim 23, wherein the operative connection is wireless.

31. The method according to claim 23, wherein instrument exposure data is provided from the instrument to the docking station, an exposure log is transmitted from the docking station to the remote service center and the remote service center transmits conclusions relative to exposure to the docking station.

32. The method according to claim 23, wherein the instrument monitors air in breathing equipment.

33. The method according to claim 23, wherein the instrument monitors water quality.

34. The method according to claim 23, wherein the instrument monitors air quality.

* * * * *